United States Patent [19]

Koch

[11] Patent Number: 4,892,539
[45] Date of Patent: Jan. 9, 1990

[54] VASCULAR GRAFT

[75] Inventor: Durmus Koch, Demarest, N.J.

[73] Assignee: D-R Medical Systems, Inc., Northvale, N.J.

[21] Appl. No.: 152,978

[22] Filed: Feb. 8, 1988

[51] Int. Cl.$^4$ .......................... A61F 2/06; A61F 2/04; D03D 3/02

[52] U.S. Cl. ................... 623/1; 139/387 R; 600/36; 606/155

[58] Field of Search .............. 623/1, 11, 12; 128/334 R; 139/387 R, 388; 600/36

[56] References Cited

U.S. PATENT DOCUMENTS

| | | |
|---|---|---|
| 2,127,903 | 8/1938 | Bowen . |
| 3,142,067 | 7/1964 | Liebig ................................ 623/1 |
| 3,254,651 | 6/1966 | Collito . |
| 3,304,557 | 2/1967 | Polansky .................... 139/387 R |
| 3,316,557 | 5/1967 | Liebig . |
| 3,479,670 | 11/1969 | Medell . |
| 3,805,301 | 4/1974 | Liebig . |
| 3,945,052 | 3/1976 | Liebig . |
| 4,047,252 | 9/1977 | Liebig et al. . |
| 4,164,045 | 8/1979 | Bokros et al. . |
| 4,190,909 | 3/1980 | Ablaza . |
| 4,193,137 | 3/1980 | Heck . |
| 4,208,745 | 6/1980 | Okita . |
| 4,229,838 | 10/1980 | Mano . |
| 4,250,138 | 2/1981 | Okita . |
| 4,282,011 | 8/1981 | Terpay . |
| 4,304,010 | 12/1981 | Mano . |
| 4,306,318 | 12/1981 | Mano et al. . |
| 4,313,231 | 2/1982 | Koyamada . |
| 4,321,914 | 3/1982 | Begovac et al. . |
| 4,501,263 | 2/1985 | Harbuck . |
| 4,517,687 | 5/1985 | Liebig et al. ..................... 623/1 |
| 4,530,113 | 7/1985 | Matterson . |

OTHER PUBLICATIONS

Vascular Surgery, Rutherford, 1984, pp. 384, 385, 387 and 389.
Biologic and Synthetic Vascular Prosthesis, Stanley, 1982, pp. 143, 144, 145, FIGS. 9-10, 9-12, 148, 181, 182, 210, 211, 487-490, 509-520 and 525.
Vascutek Triaxial not dated.
Bifurcated Gore—Tex Vascular Graft not dated.
Gore—Tex Suture (4 pages) ©1986.
Gore—thinner with even better handling ©1984.
Bard—Be prepared ©1987.
Inter Vascular—Which Graft not dated.

Primary Examiner—Alan W. Cannon
Attorney, Agent, or Firm—Donald Brown

[57] ABSTRACT

A vascular tubular graft of a woven fabric with a single velour outside (external) surface and a smooth interior surface, said outside surface having a plurality of loops, each loop extending around a portion of the circumference thereof and each loop formed by fill yarn positioned about warp yarn.

16 Claims, 1 Drawing Sheet

VASCULAR GRAFT

BACKGROUND OF THE DISCLOSURE

This invention is directed to vascular grafts of synthetic fibers. Vascular grafts (prothesis) are currently used to replace certain diseased arteries by joining e.g., by sewing the ends of the vascular tubular grafts to the remaining portions of the artery e.g., human artery. Operations for this purpose are commonly done by surgeons who first remove the diseased portion of the artery, e.g., blocked by a clot, and then implant the graft in its place. Alternatively, the graft may be used as a bypass around a diseased vessel. Such grafts usually are used in connection with arteries which carry large blood volumes e.g., located in the lower body of the human, although it may be used in other parts of the human body. Grafts which are presently in use are of a woven or knitted construction. Knitted construction grafts tend to be of high porosity and thus bleeding often accompanies their use. While woven grafts are in wide use, there is still a need for a new and improved woven graft that because of its weave construction is of low porosity, is smooth on the interior of the graft to prevent obstruction thereof by various material carried by the blood in the graft, and provides a staggered design outer looped surface extending around the circumference thereof to allow for the body tissue which grows thereabout after implantation to firmly support it in the body. The graft is also preferably crimped so that it will not kink easily during implantation.

PRIOR WORK IN THE FIELD

The following U.S. Pat. Nos. may be referred to which show the state of the art: 4,517,687; 4,047,252; 4,501,263; 4,164,045; 4,229,838; 3,316,557; 3,945,052; 4,190,909; 4,304,010; 2,127,903; 4,313,231; 4,208,745; 4,530,113; 4,193,137; 3,254,651; 3,479,670; and 4,306,318. Patents relating to plastics which may be of interest include No. 4,250,138 and No. 4,321,914. Reference may also be had to the following articles: "A New Woven Double Velour Vascular Prosthesis", Stewart Scott et al, J. Cardionvasc, Surg. 26, 1985 and "Aortoiliac Reconstruction with Dacron Double Velour", S. M. Lindenauer et al, J. Cardiovasc, Surg., 25, 1984, which also shows the state of the art and the utility of vascular grafts.

BRIEF DESCRIPTION OF THE DISCLOSURE

The invention is directed to a woven velour synthetic tubular graft (straight or bifurcated) preferably of polyester such as polyethylene terephthalate having a velour structure as its outer surface and a plain weave as its inner surface. The velour structure at the outer surface is provided by the fill yarn rather than the warp yarns. The differentiation between the inner surface (plain weave) and the outer velour surface is accomplished by having the filling yarn interlacing with the warp yarns at different patterns preferably every other pick. For example, if the weaving started with a plain weave, the next interlacing pick is a velour-generating pick, which extends over a predetermined number of warp ends before interfacing with a single end of warp. The yarn used is preferably of polyester and the especially preferred yarn used are made by Dupont under the Trademark DACRON. Type 56 Dacron yarn is the most preferred for both the fill and warp yarns, however, comparable yarns and fibers may be used as will be apparent to those skilled in the art. The yarn may be used as textured or untexturized with texturized being preferred. The purposes of the outer velour is to provide a base for rapid internal human body tissue growth about the velour circumferential loops thus securing the position of the graft and the smooth inner surface is provided to prevent formations of obstructions on the interior wall of the graft. In addition, because the velour is in the fill position, the process for crimping of the graft will not affect the structure of the velour and will not cause the velour loop to fold or elongate and thus weaken the graft. In this invention the warp yarns run lengthwise in the tubular graft and are crossed by the fill yarn. The fabric of this invention is tightly woven and of low porosity in order to prevent bleeding through the graft after implantation.

The graft may be a straight tubular shape for connection to a single artery to replace a diseased section, or for replacing a three arm connection i.e., connection to three arteries, the graft may be made in bifurcated form.

Before implantation, the graft is preclotted with the patients blood to make it impervious to bleeding. Because the graft has a smooth inner surface, it will not pick up excessive clotting material from the blood which is likely to be a precursor to an obstructed graft after implantation. Also, with the smooth inner surface the possibility of a clot forming in the graft and being released in the blood stream is decreased.

DETAILED DESCRIPTION OF THE DISCLOSURE

Figure 1:
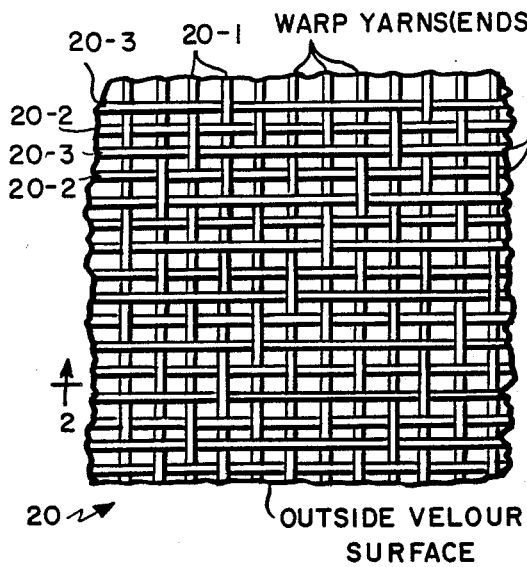
FIG. 1 is a top plan view of the woven fabric as used in accordance with the present invention to show the velour outer surface pattern.
Figure 3:
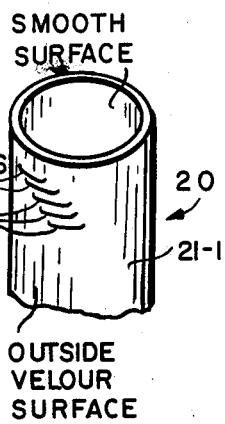
FIG. 3 is a tube made of the fabric of FIG. 1.
Figure 2:
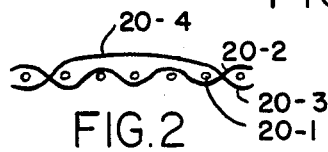
FIG. 2 is a sectional view taken along line 2—2 FIG. 1.

Reference should now be made to FIGS. 1, 2 and 3 which show the fabric of the invention (FIG. 1) which is formed into a tube 21 for use as a graft. In FIG. 1 the warp yarns are shown at 20-1 and the fill yarn is shown having portions 20-2 and 20-3. Fill yarn portion 20-2 is shown in a plain weave pattern with the fill yarn interlacing with the warp yarns as shown in an under and over plain weave fashion. The velour in the fabric is formed by interlacing of the fill yarn portion 20-3 which forms a velour pattern having outside loops 20-4 which float (extend) over five warp yarn ends 20-1 as shown.

The next velour loop pattern formed by fill yarn portion 20-3, after the next regular weave pattern formed by fill yarn portion 20-2, is then staggered one warp yarn to form the weave pattern of FIG. 1. The weaving is continued one yarn at a time for the entire pattern to form the staggered velour loops 20-4 (see FIG. 3) which is provided around the outer circumference of the tube 21 formed of the fabric 20. As shown in FIG. 1 the loops 20-4 preferably extend over 5 warp yarns, however, in the practice of the invention, loops of fill yarn which extend over 4 to 8 warp yarns are quite acceptable.

In order to form the tube of the invention e.g., Dacron brand type 56 yarn 80 Denier/47 filament is preferably used for both the warp yarns and fill yarn. The yarns are preferably texturized on a standard false twist texturing machine. After texturizing, the yarn is wrapped (wound) about one another to form from the 50 Danier/47 filament yarn, a 100 Danier/94 filament warp yarn with 5 turns per inch twist. The fill yarn is similarly formed except it only has 1 to 2 turns per inch of twist. Thereafter the fabric of FIG. 1 is woven in a conventional manner using a loom as known in the art. The woven outer (external) velour fabric 20 is preferably formed using 160 ends per inch for warp and 130 picks per inch in the fill position. The tube that is usually formed is about 6 to 38 mm in diameter depending upon the use intended, however it may be made in various lengths e.g., 90 to 20 cm.

Thereafter the woven tube such as shown in FIG. 3 is washed to remove oils and other materials using conventional washing agents e.g., a mixture of 3 parts Hyponic OP55 agent (Diamond Shamrock) and 1 part Syntergist TER-1 (Diamond Shamrock) agent mixed with water (temperature 165° F. to 180° F.) in the ratio of 3% washing agents and 97% water. During this washing the tube 21 will shrink.

Figure 4:
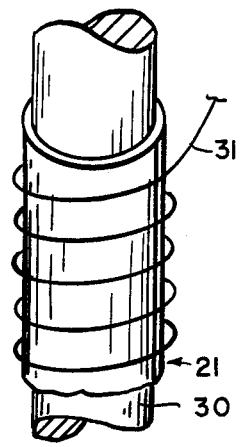
FIG. 4 is view showing the first step in forming circumferential crimp in the fabric tube of FIG. 3.
Figure 5:
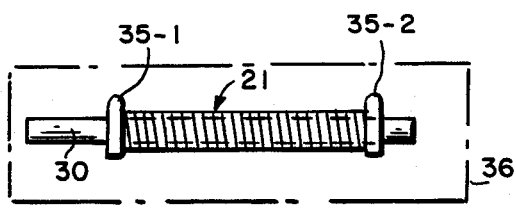
FIG. 5 is view showing the second step in forming the crimp in the fabric tube of FIG. 3.
Figure 6:
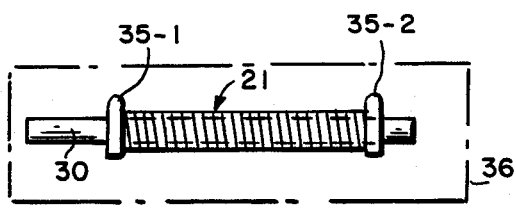
FIG. 6 is view showing the third step in forming the crimp of the tube of FIG. 3.

After washing, the woven tube 21 is placed over a mandrel 30 as shown in FIG. 4 in a tight fit. The tube is then wrapped with a plastic monofilament 31 (e.g., nylon, about 0.015 inches diameter) about 10 turns per inch. The wrapped tube 21 is then placed in a machine (see FIG. 5) comprising two posts 33-1 and 33-2 holding the mandrel positioned on support 32. The posts 33-1 and 32-1 are both moved as shown by the arrows to compress the tube from both ends from e.g., 60 to 20 cm. The monofilament 31 is then removed from about the tube 21. Thereafter the compressed tube is positioned in an oven 36 on the mandrel 30 and held in place by clips 35-1 and 35-2. The tube is heated for 30 minutes at 250° F. At this time, the tube is removed from the oven, taken off the mandrel 31 and placed over a smaller diameter mandrel about 1 to 2 mm in diameter less than the first mandrel. The product is then streched e.g., by hand to 40 cm in length so that the crimp is not as dense. Thereafter, the crimped tube 21 is again placed in the oven at 250° F. for 30 minutes to form the final shape as shown in FIG. 7.

Figure 7:
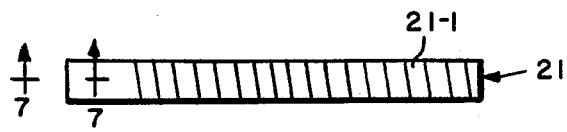
FIG. 7 shows the finished woven external velour graft in straight (tube) form of the invention.
Figure 8:
FIG. 8 is a section taken along line 7—7 in FIG. 7 in order to show the crimp in the outer wall.
Figure 9:
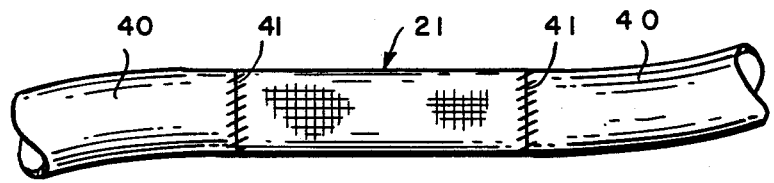
FIG. 9 is a view showing the graft sewn to repair an artery.
Figure 10:
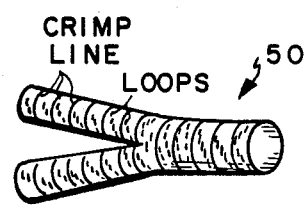
FIG. 10 is a view showing the graft of this invention in a bifurcated form.

FIGS. 7 and 8 show the final product after crimping with the looped velour outer surface 21-1 and inner smooth surface 21-2. In FIG. 9 there is shown the graft 21 sewn by surgical thread 41 to an artery 40 after the diseased artery section has been surgically removed. FIG. 10 shows the final product 50 having the same weave construction and crimp as the tube shown in FIGS. 1 to 9 in a bifurcated form (Y) for connection to three artery branches e.g., aorta to the left and right iliac arteries.

As is customery, the graft is immersed in the blood of the patient to preclot it prior to use as shown in FIG. 9.

It is to be understood that other conventional methodology may be used to fabricate the graft as would be apparent to those skilled in the art.

It is also to be understood that multiple fill yarns instead of a single fill yarn may be used to weave the products of the invention. It is also to be understood that in addition to a single fill on a second shuttle of a loom, that multiple fill yarns on a single shuttle or on multiple shuttles may be used to weave the tubes of the invention. The use of multiple yarns on multiple shuttling will afford the opportunity to vary tension and type of yarn from shuttle to shuttle.

I claim:

1. A vascular graft comprising a seamless tube of crimped woven texturized yarn fabric, said tube having a complete outer velour surface and a smooth inner surface, said outer velour surface having loops open to receive tissue ingrowth formed of fill yarn, each of said loop extending outside of a plurality of warp yarns.

2. The graft of claim 1 in which the fill yarn is also positioned about warp yarns in a plain pattern, said plain pattern being positioned between adjacent fill yarn forming the loops.

3. A hollow tubular graft comprising a single outer woven complete velour fabric from warp yarns and fill yarn, said warp yarns supporting a plurality of first fill yarn portions, said first fill yarn portions are positioned outside of warp yarns to from only outer circumferential loops exclusive of inner circumferencial loop with the loops each extending outside of 4 to 8 warp yarns and the adjacent second fill yarn portions woven so they are offset from one another at least one warp yarn so that adjacent loops along the length of the tubular graft are out of alignment, said loops being substantially transverse to the longitudinal axis of the tube.

4. The graft according to claim 1 in which the yarns are polyester.

5. The graft of claim 3 which is crimped.

6. The graft of claim 3 in which the yarns are texturized.

7. The graft of claim 3 in which the yarns are untexturized.

8. The graft of claim 1 in which the yarns are polyester.

9. The graft of claim 1 in which the yarns are polyethylene terephthlate.

10. The method of repairing an artery comprising connecting the graft of claim 1 to an artery.

11. The method of repairing an artery comprising connecting the graft of claim 3 to an artery.

12. A vascular tubular graft of a woven synthetic fibers with a complete velour external surface and a smooth interior surface, said external surface having a plurality of loops, each loop extending around a portion of the circumference of the graft and each loop formed by fill yarn positioned externally of warp yarns, said loops being substantially transverse to the longitudinal axis of the tubular graft and the warp yarns are in substantially the same direction as the longitudinal axis of the tubular graft.

13. The graft of claim 11 in which each loop along the length of the tubular graft is offset and out of alignment with the next adjacent loop.

14. The graft of claim 1, 3 or 12 which is in a straight or bifurcated form.

15. The method of claim 10 in which the graft is in straight or bifurcated form.

16. The graft of claim 12 in which the tubular graft is crimped about its circumference.

* * * * *